(12) United States Patent
Pellerin et al.

(10) Patent No.: US 11,768,160 B2
(45) Date of Patent: Sep. 26, 2023

(54) MULTIPARAMETER STANDARD SOLUTION FOR WATER-QUALITY ANALYSIS

(71) Applicant: UNITED STATES GEOLOGICAL SURVEY, Reston, VA (US)

(72) Inventors: Brian Anthony Pellerin, Herndon, VA (US); Angela Merleen Hansen, Sacramento, CA (US)

(73) Assignee: U.S. Geological Survey, Reston, VA (US)

( * ) Notice: Subject to any disclaimer, the term of this patent is extended or adjusted under 35 U.S.C. 154(b) by 392 days.

(21) Appl. No.: 17/100,859

(22) Filed: Nov. 21, 2020

(65) Prior Publication Data

US 2021/0372941 A1 Dec. 2, 2021

Related U.S. Application Data

(60) Provisional application No. 63/031,228, filed on May 28, 2020.

(51) Int. Cl.
*G01N 21/00* (2006.01)
*G01N 21/93* (2006.01)
*G01N 33/18* (2006.01)

(52) U.S. Cl.
CPC ............. *G01N 21/93* (2013.01); *G01N 33/18* (2013.01); *G01N 2201/12715* (2013.01); *G01N 2201/12746* (2013.01); *G01N 2201/13* (2013.01)

(58) Field of Classification Search
CPC .................. G01N 21/93; G01N 33/18; G01N 2201/12715; G01N 2201/12746; G01N 2201/13

(Continued)

(56) References Cited

U.S. PATENT DOCUMENTS

2003/0042149 A1* 3/2003 Smith .................... G01N 33/18
205/775
2008/0240543 A1* 10/2008 Budach ................ G01N 21/645
382/141

(Continued)

FOREIGN PATENT DOCUMENTS

CN 101052762 A * 10/2007 ............. C09B 56/14
JP 2001228139 A * 8/2001
JP 2006184148 A * 7/2006

OTHER PUBLICATIONS

Bergamaschi, B.A., Fleck, J.A., Downing, B.D., Boss, E., Pellerin, B., Ganju, N.K., Schoellhamer, D.H., Byington, A.A., Heim, W.A., Stephenson, M., and Fujii, R., 2011, Methyl mercury dynamics in a tidal wetland quantified using in situ optical measurements. Limnology and Oceanography, v. 56, No. 4, p. 1355-1371.

(Continued)

*Primary Examiner* — Max H Noori
(74) *Attorney, Agent, or Firm* — James Mitchell

(57) ABSTRACT

A multiparameter standard solution for verifying and calibrating water quality sensors containing an aqueous pH buffer, a xanthene dye, and distyryl biphenyl (DSBP) is provided. The standard solution provides a safe, quick, easy, and stable field standard to simultaneously conduct calibration analysis for several sensors at once. The standard solution is stable when stored and can be safely disposed of in the field. Methods of calibrating sensors used in water quality analysis using the multiparameter standard solution are also provided.

20 Claims, 4 Drawing Sheets

(58) Field of Classification Search
USPC .......................................................... 73/1.03
See application file for complete search history.

(56) References Cited

U.S. PATENT DOCUMENTS

| | | | |
|---|---|---|---|
| 2009/0107917 A1* | 4/2009 | Capehart ................... | C02F 9/00 210/207 |
| 2011/0246118 A1* | 10/2011 | Tokhtuev ............. | G01N 21/645 702/104 |
| 2013/0264291 A1* | 10/2013 | Itzhak ................... | C02F 1/4674 210/96.1 |
| 2018/0105438 A1* | 4/2018 | Elliott ................ | G02B 19/0095 |
| 2018/0275037 A1* | 9/2018 | Favero ................. | E21B 21/062 |
| 2019/0084843 A1* | 3/2019 | Möller .................... | C02F 1/283 |
| 2019/0271615 A1* | 9/2019 | Trumbo ............. | G01N 33/1826 |
| 2021/0181167 A1* | 6/2021 | Sundstrom ................ | C02F 1/42 |
| 2022/0233045 A1* | 7/2022 | Karren .................... | A47L 11/34 |
| 2022/0248924 A1* | 8/2022 | Karren ................. | C02F 1/4618 |

OTHER PUBLICATIONS

Bergamaschi, B.A., Fleck, J.A., Downing, B.D., Boss, E., Pellerin, B.A., Ganju, N.K., Schoellhamer, D.H., Byington, A. A., Heim, W.A., Stephenson, M., and Fujii, R., 2012, Mercury Dynamics in a San Francisco Estuary Tidal Wetland. Assessing Dynamics Using In Situ Measurements: Estuaries and Coasts, v. 35, No. 4, p. 1036-1048.

Downing, B.D., Boss, E., Bergamaschi, B.A., Fleck, J.A., Lionberger, M.A., Ganju, N.K., Schoellhamer, D.H., and Fujii, R., 2009, Quantifying fluxes and characterizing compositional changes of dissolved organic matter in aquatic systems in situ using combined acoustic and optical measurements. Limnology and Oceanography—Methods, v. 7, p. 119-131.

EXO User Manual—Advanced Water Quality Monitoring Platform (Item # 603789 REF).

Gibs, J., Wilde, F.D., and Heckathorn, H.A., 2007, U.S. Geological Survey National Field Manual for the Collection of Water-Quality Data, Field Measurements, Chapter A6 Section 6.8.

Hansen, A.M., Fleck, J.A., Kraus, T.E.C., Downing, B.D., von Dessonneck, T., and Bergamaschi, B.A., 2018, Procedures for using the Horiba Scientific Aqualog® fluorometer to measure absorbance and fluorescence from dissolved organic matter. U.S. Geological Survey Open-File Report 2018-1096, p. 31.

Pellerin, B.A., Downing, B.D., Kendall, C., Dahlgren, R.A., Kraus, T.E.C., Saraceno, J., Spencer, R.G.M., and Bergamaschi, B.A., 2009, Assessing the sources and magnitude of diurnal nitrate variability in the San Joaquin River (California) with an in situ optical nitrate sensor and dual nitrate isotopes. Freshwater Biology, v. 54, No. 2, p. 376-387.

Pellerin, B.A., Bergamaschi, B.A., Downing, B.D., Saraceno, J.F., Garrett, J.A., and Olsen, L.D., 2013, Optical techniques for the determination of nitrate in environmental waters: Guidelines for instrument selection, operation, deployment, maintenance, quality assurance, and data reporting. U.S. Geological Survey Techniques and Methods 1-D5, p. 37.

Saraceno, J.F., Pellerin, B.A., Downing, B.D., Boss, E., Bachand, P.A.M., and Bergamaschi, B.A., 2009, High-frequency in situ optical measurements during a storm event: Assessing relationships between dissolved organic matter, sediment concentrations, and hydrologic processes. Journal of Geophysical Research—Biogeosciences, v. 114.

Spencer, R.G.M., Pellerin, B.A., Bergamaschi, B.A., Downing, B.D., Kraus, T.E.C., Smart, D.R., Dahgren, R.A., and Hemnes, P.J., 2007, Diurnal variability in riverine dissolved organic matter composition determined by in situ optical measurement in the San Joaquin River (California, USA). Hydrological Processes, v. 21, No. 23, p. 3181-3189.

Wagner, R.J., Boulger, R.W., Jr., Oblinger, C.J., and Smith, B.A., 2006, Guidelines and standard procedures for continuous water-quality monitors—Station operation, record computation, and data reporting. U.S. Geological Survey Techniques and Methods 1-D3, p. 51.

Watras, C.J., Hanson, P.C., Stacy, T.L.., Morrison, M., Mather, J., Hu, Y.H., and Milewski, P., 2011, A temperature compensation method for CDOM fluorescence sensors in freshwater: Limnology and Oceanography—Methods, v. 9, p. 296-301.

* cited by examiner

MULTIPARAMETER STANDARD SOLUTION FOR WATER-QUALITY ANALYSIS

RELATED APPLICATION DATA

This application claims the benefit of priority of U.S. Provisional Patent Application No. 63/031,228 filed on May 28, 2020, the contents of which are incorporated by reference herein in its entirety.

FIELD OF THE INVENTION

The present disclosure generally relates to the field of surface water quality monitoring and data collection, such as freshwater streams, lakes, and estuaries. In particular, the present disclosure is directed to a multi-parameter standard solution for testing and calibrating water quality sensors.

BACKGROUND OF THE INVENTION

This section introduces aspects that may help facilitate a better understanding of the invention. Accordingly, the statements of this section are to be read in this light and are not to be understood as admissions about what is prior art or what is not prior art.

The use of field sensors to monitor water quality requires adherence to methods that ensure the consistent and accurate collection of data. The sensors that are used to measure water quality parameters require careful field observation, cleaning, and calibration procedures. Sensor calibration and field validation are critical steps in evaluating instrument performance, identifying necessary corrections to be applied to field data, and ensuring that data are comparable across sites and sensors. Good practice methods require that instruments be tested and the sensors calibrated before each field use. Calibrations are typically performed in the field in preparation for making measurements.

As new sensors are developed and put into operation, new calibration methods are needed to ensure that the data meet established criteria. Given the goal of making comparable measurements across sites and over time, there is a clear need to define standard solutions and protocols for sensor calibration and field checks, specifically to identify primary standards to be used in laboratory sensor calibrations and secondary-check standards to evaluate sensor performance in the lab or field. Secondary standards, in particular, need to be safe to handle in the field, stable, and relatively insensitive to changes in temperature.

Primary and secondary standards are used for accurate calibration and validation of field fluorometers. Primary standards are substances in the purest form and are used for robustly quantifying unknown concentrations, including calibrating secondary standards. Primary standards are used for the initial characterization of the sensor (typically by the manufacturer) but are not conducive to routine use in field applications due to issues with high costs, solvents used, and difficulties in maintaining purity. Secondary standards include a variety of dyes and solid materials that are relatively inexpensive, more stable and easier-to-use alternatives to primary standards for verifying sensor operation.

Techniques and methods used for the field collection of water quality data using in situ sensors are described (e.g., Wagner et al., 2006; Pellerin et al., 2013). On the forefront of emerging water-quality sensor technologies are fluorescence-based optical sensors, designed specifically to measure the fluorescent component of dissolved organic matter (DOM) when exposed to near-ultraviolet light. DOM includes a broad range of organic molecules of various sizes and composition that are released by all living and dead plants and animals. Measuring the fraction of light absorbed at specific wavelengths and subsequently released at longer wavelengths (i.e., fluorescence) is diagnostic of dissolved organic matter type and amount.

An advantage of using fluorescence to measure DOM is that it is more sensitive than absorption methods. Also, the excitation and emission spectra show greater detail and provide more information on chemical composition than do absorbance. Accordingly, optical sensors measuring the fluorescent fraction of DOM (fDOM) have gained popularity for use as a proxy for dissolved organic matter concentration (Spencer et al., 2007; Downing et al., 2009; Pellerin et al., 2009; Saraceno et al., 2009) and other dissolved constituents that are commonly associated with DOM such as mercury species (Bergamaschi et al., 2011; Bergamaschi et al., 2012).

Typically, raw fDOM sensor output is calibrated to quinine sulfate (QS), a colorless solution in acid that has a peak fluorescence at excitation 350 nm and emission 450 nm, which is similar to DOM and is within the spectral window where fDOM sensors generally measuring fluorescence. The units of fDOM are often expressed as quinine sulfate units (QSU), where I QSU=1 ppb quinine sulfate, or in Relative Fluorescence Units (RFU).

Although there is a long history of QS as a calibration standard, there are several reasons that make QS impractical and unsafe for field use:
  (i) QS is difficult to prepare accurately at low concentrations relevant to natural waters (e.g. <300 ppb);
  (ii) The QS solution needs to be prepared using a dilution of concentrated sulfuric acid which presents a health hazard and requires hazardous waste disposal; and
  (iii) QS degrades quickly (i.e. <5 days), particularly when exposed to UV light, requiring solutions to be made frequently.

Similarly, chlorophyll-a (Chl-a) fluorescence sensors are becoming widely used as a surrogate for phytoplankton concentration or biomass. Chlorophyll-a has a primary absorption peak in the blue (465 nm) part of the visible light spectrum and a smaller secondary peak in the red (665 nm) which can be detected by field fluorometers. Secondary standards from a variety of materials have been used for algal fluorometers. In particular, rhodamine dye (e.g. Rhodamine WT) has been used due to its high solubility in water, known optical properties, and long-term stability when stored in the dark at room temperature. Chl-a fluorescence sensors generate data in RFU format and an estimated pigment concentration in ug/L.

Additional sensors commonly used in water quality analysis include sensors for specific conductivity, temperature, dissolved oxygen, pH, oxidizing-reducing potential, and turbidity. As additional sensors are grouped for in situ monitoring, field calibration checks are becoming quite time consuming for even the basic set of sensors that require ongoing verification over timescales ranging from weekly to semi-annual intervals (i.e. pH, fDOM, Chl-a, specific conductivity, turbidity). As such, a need exists for simple, fast, and effective methods to verify the calibration of water quality field sensors and to standardize measurements among the sensors and across the landscape. A particular need exists for an alternative to QS for use in an accurate and effective fDOM sensor calibration standard that can be applied to field sensors, is environmentally safe, and is stable.

SUMMARY OF THE INVENTION

The description below describes a multiparameter standard solution for verifying and calibrating water quality sensors. According to various embodiment, the multiparameter standard solution provides a single solution for verifying and calibrating multiple sensors used in water quality analysis including fDOM, chlorophyll-a, and pH. Embodiments of the multiparameter standard solution containing a combination of a xanthene dye, distyryl biphenyl (DSBP), and a pH buffer provide a quick, easy, and stable field standard solution to conduct calibration analysis for several sensors, including optical and fluorescence sensors. The differences in the fluorescent peaks between the xanthene dye and DSBP correspond to the excitation and emission wavelengths and bandpass of the fluorescence sensors and show no evidence of cross-talk between sensors and standards. In addition, the effects of temperature on the fluorescence properties of the standard solution is linear and can be easily corrected for.

The present multiparameter standard solution and its components are stable for at least 90 days stored at room temperature in the dark. The standard solution can also be safely disposed of in the field, keeping in mind areas that may contain biota sensitive to the pH of the buffer (i.e. pH 10) or where future sampling for wastewater indicators or pesticides may occur.

In the field of water quality measurement and analysis, embodiments of the multiparameter standard solution are used with optical probes and sensors that measure fluorescent dissolved organic matter (fDOM), total algae (chlorophyll and blue-green algae) and pH. Various embodiments of the standard solution are also used as a second verification check point for fDOM, total algae, and pH sensors, and are used with a zero-standard or "zero verification" standard (e.g. organic-free water) to generate a two-point check. Various embodiments of the standard solution provide a single solution that is used to simultaneously verify calibrations for multiple sensors at once, including fDOM, chlorophyll-a, and pH sensors.

According to various embodiments of the present disclosure, a standard solution for verifying and calibrating water quality sensors contains an aqueous pH buffer, a xanthene dye, and distyryl biphenyl (DSBP). The standard solution has known properties that can be accurately measured such as pH and fluorescence at determined excitation wavelengths. In some embodiments, the standard solution contains an aqueous pH 10 buffer, a rhodamine dye such as rhodamine WT, and disodium 4,4'-bis(2-sulfostyryl)biphenyl.

According to various embodiments of the present disclosure, a method of verifying or calibrating a sensor used in water quality analysis includes: contacting the sensor with a standard solution containing an aqueous pH buffer, a xanthene dye, and distyryl biphenyl (DSBP), the standard solution having one or more known property that is measurable by the sensor; analyzing the one or more property of the standard solution with the sensor and taking a calibration measurement; and determining whether or not the sensor is calibrated based on the calibration measurement. The standard solution has one or more known determined property that is measurable by the sensor and corresponds to an expected calibration measurement. The sensor includes, for example, one or more of a pH sensor, a fDOM sensor, a chlorophyll-a sensor, and a total algae sensor, and the known determined properties include, for example, pH and fluorescence at a determined excitation wavelength.

According to various embodiments of the present disclosure, a method of performing water quality analysis includes: (i) contacting a sensor used in water quality analysis with a standard solution containing an aqueous pH buffer, a xanthene dye, and distyryl biphenyl (DSBP), the standard solution having one or more known property that is measurable by the sensor; (ii) analyzing the one or more property of the standard solution with the sensor and taking a calibration measurement; (iii) determining whether or not the sensor is calibrated based on the calibration measurement; (iv) when determining that the sensor is not calibrated, adjusting the sensor and repeating steps (i)-(iii), and when determining that the sensor is calibrated, performing steps (v-vi); (v) contacting the calibrated sensor with a sample for water quality analysis; and (vi) analyzing the sample for water quality.

BRIEF DESCRIPTION OF THE DRAWINGS

The objects, features and advantages of the present disclosure will become more apparent from the following detailed description and the accompanying drawings.

An appreciation of the disclosure and many attendant advantages thereof may be understood by reference to the accompanying drawings. Included in the drawings are the following figures.

DETAILED DESCRIPTION OF THE INVENTION

Figure 1:
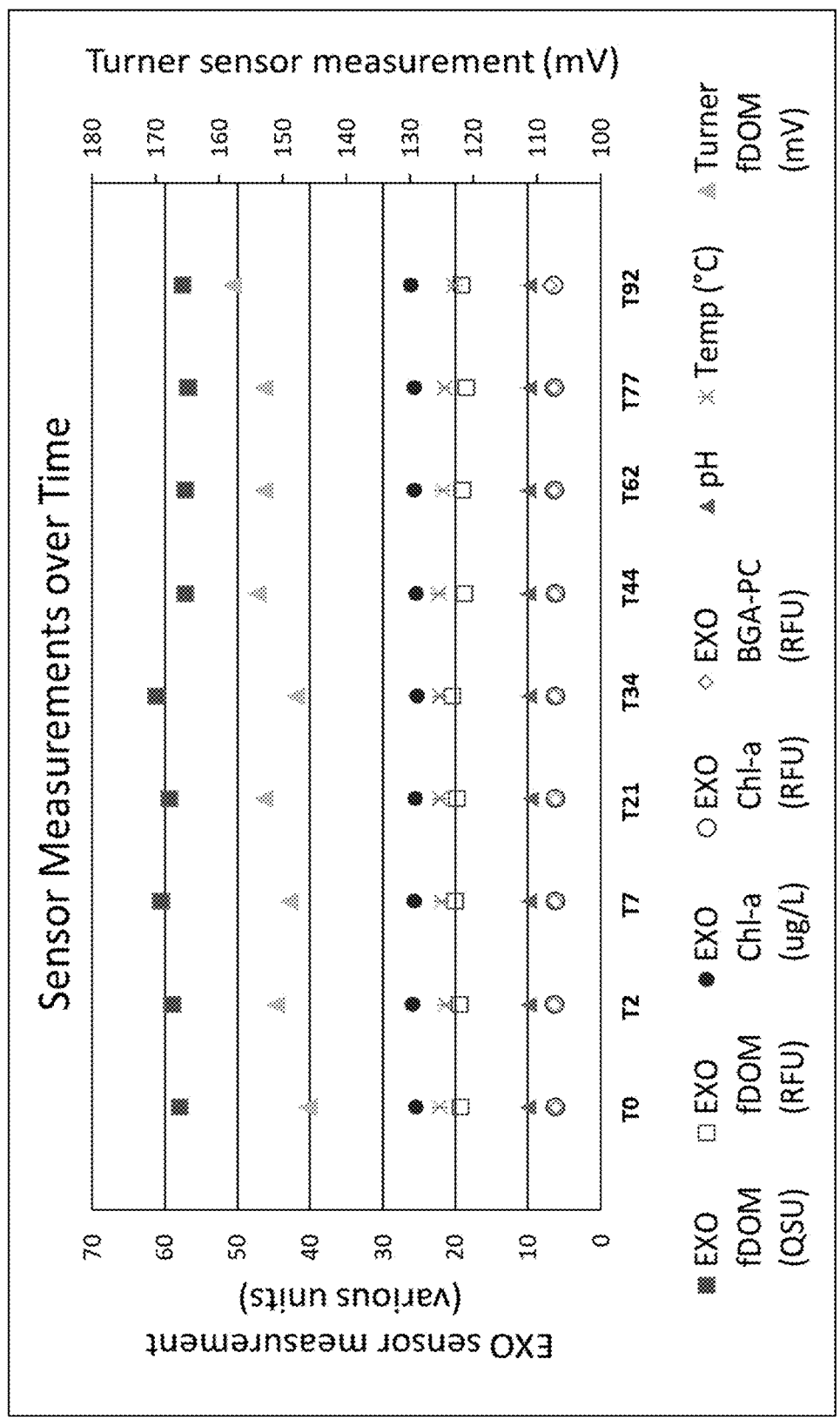
FIG. 1 is a graph of sensor measurements over time measured with an EXO multiparameter sonde or with a Turner sensor. T=Time (day of sensor measurement); fDOM=Fluorescent Dissolved Organic Matter, QSU=Quinine Sulfate Unit, RFU=Relative Fluorescence Unit; Chl-a=Chloroform-a; BGA=Blue Green Algae; PC=Phycocyanin; mV=milliVolt. Each data point represents a single measurement made by each sensor on each particular day.

While the invention will be described in conjunction with embodiments, the invention can be applied to a wide variety of applications, and the description herein is intended to cover alternative, modifications and equivalents within the spirit and scope of the invention and the claims. The description in the present disclosure should not be viewed as limiting or as setting forth the only embodiments of the invention, as the invention encompasses other embodiments not specifically recited in this description.

As used herein, the singular forms "a" "an" and "the" are intended to include the plural forms as well, unless the context clearly indicates otherwise. It further will be understood that the terms "comprises" "comprising" "includes"

and/or "including" specify the presence of stated features, steps, or components, but do not preclude the presence or addition of one or more other features, steps, or components. It also should be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

The present disclosure is directed toward all novel and non-obvious features and aspects of the various disclosed embodiments. Any theories of operation are to facilitate explanation, but the disclosed methods and devices are not limited to such theories of operation.

According to various embodiments, the present disclosure is directed to a multiparameter calibration standard solution for water quality sensors. The standard solution contains an aqueous pH buffer, a xanthene dye, and distyryl biphenyl (DSBP) and provides a single solution useful to verify and calibrate water quality sensors that are part of a system to measure the pH, phytoplankton concentration or biomass, and amount of dissolved organic matter in a water sample taken from the field. Embodiments of the standard solution are used to calibrate optical sensors, such as fluorescence optical sensors.

According to various embodiments, the multiparameter standard solution contains an aqueous pH buffer. In some embodiments, the pH buffer is a pH 10 buffer, although the standard solution is not strictly limited to pH 10 and can include a buffer in a range of about pH 9-11. In some embodiments, the pH buffer is a buffer calibration solution or a pH standard buffer. Such pH buffers that are NIST (National Institute of Standards and Technology) buffers or are traceable to primary standards set by NIST are known in the art. NIST buffers include pH 9.18 buffers and commercially available NIST traceable buffers include pH 10.01 buffers (e.g., ThermoFisher Scientific Inc., Waltham, MA) that are also known in the art as USA buffers. Embodiments of the standard solution contain a dye-free pH buffer.

According to various embodiments, the present multiparameter standard solution contains a xanthene dye, such as a rhodamine dye or a rhodamine derivative dye. Various rhodamine derivatives are known in the art, such as Rhodamine B, Rhodamine 6G, Rhodamine 123, and Rhodamine WT. In one or more embodiments, the standard solution contains Rhodamine WT. Those skilled in the art consider Rhodamine WT to be a compound characterized by its ease of use, relatively low cost, low adsorptive tendency, strong fluorescence, high diffusivity, chemical stability, and benign character in the aquatic environment.

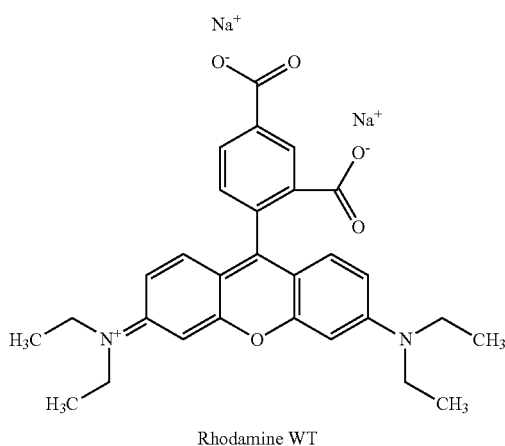 [SMILES: [Na+] ; CCN(CC)c1ccc2c(-c3ccc(C(=O)[O-])cc3C(=O)[O-])c3ccc(=[N+](CC)CC)cc-3oc2c1 ; [Na+]]

Rhodamine WT

According to various embodiments of the present multiparameter standard solution, the solution includes distyryl biphenyl (DSBP) or a derivative thereof. In some embodiments of the standard solution, the DSBP is a 4,4'-distyryl biphenyl, or a salt or a derivative thereof. In some embodiments, the DSBP is disodium 4,4-bis(2-sulfostyryl)biphenyl, or benzenesulfonic acid, 2,2'-([1,1'-biphenyl]-4,4'-diyldi-2,1-ethenediyl)bis-, disodium salt (CAS 27344-41-8), or an alternative salt thereof.

In one or more embodiments, the DSBP is commercially available as TINOPAL® CBS-X (BASF).

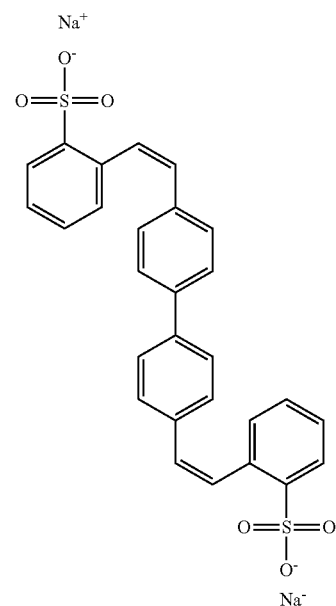

Disodium 4,4'-bis(2-sulfostyryl)biphenyl

Embodiments of the multiparameter standard solution include a solution containing an aqueous pH buffer, a rhodamine dye, and DSBP present in concentrated amounts to form a stock solution that is typically diluted to a lower concentration for actual use. When stored in a container and protected from the light at room temperature, the stock solution and its components remain stable for 90 days or longer. The stock solution is stored, for example, in an amber bottle.

In various embodiments, the stock solution contains DSBP at a concentration in a range of about: 1-1000 parts per million (ppm); 5-500 ppm, 10-500 ppm; 10-100 ppm; or at about 50 ppm. In various embodiments, the stock solution contains rhodamine at a concentration in a range of about: 100-10,000 ppm; 500-10,000 ppm; 500-5000 ppm; 1000-5000 ppm; or at about 2000 ppm. Embodiments of the stock solution also include any combination of concentrations of DSBP and rhodamine within these ranges.

Embodiments of the multiparameter standard solution include a solution containing an aqueous pH buffer, a rhodamine dye, and DSBP present in amounts to form a working solution. The working solution contains its components at concentrations that are ready to be used in the calibration of water quality sensors. When stored in a container and protected from the light at room temperature, the working solution and its components remain stable for 90 days or longer. The working solution is stored, for example, in an amber bottle.

In various embodiments, the working solution contains DSBP at a concentration in a range of about: 0.1-500 parts per billion (ppb); 0.5-100 ppb; 1-50 ppb; or at about 5 ppb. In various embodiments, the working solution contains rhodamine at a concentration in a range of about: 1-10,000 ppb; 10-5000 ppb; 10-1000 ppb; or at about 200 ppb. Embodiments of the working solution also include any combination of concentrations of DSBP and rhodamine within these ranges.

Embodiments of the present disclosure include a method of verifying or calibrating a sensor used in water quality analysis. The method includes contacting the sensor with a standard solution containing an aqueous pH buffer, a xanthene dye, and distyryl biphenyl (DSBP), the standard solution having one or more known property that is measurable by the sensor; analyzing the one or more property of the standard solution with the sensor and taking a calibration measurement; and determining whether or not the sensor is calibrated based on the calibration measurement. In embodiments, the one or more known property of the standard solution includes pH and fluorescence at determined excitation wavelengths, and analyzing the property includes taking calibration measurements of the property.

In embodiments, the method includes adjusting one or more sensors to correct or calibrate the sensor. After determining that the sensor is not calibrated based on the calibration measurement, the non-calibrated sensor is adjusted. Then, the steps of contacting the sensor with the standard solution, analyzing the properties of the standard solution with the sensor and taking a calibration measurement, and determining whether or not the sensor is calibrated based on the calibration measurement are repeated. Embodiments include repeating these steps until the sensor is calibrated. In some embodiments, the user determines that the sensor cannot be calibrated and that the sensor is faulty or needs replacing.

According to various embodiments of the method, the sensor is a pH sensor. According to various embodiments of the method, the sensor is an optical sensor. In a broad sense, an optical sensor converts light, or a change in light into an electronic signal. It measures the physical quantity of light and then translates it into a form that is readable by an instrument. An optical sensor is generally part of a larger system that integrates a source of light, a measuring device, and the optical sensor.

According to various embodiments, the method utilizes at least two different types of sensors and the sensors include one or more of a pH sensor, a total algae sensor, and a fDOM sensor. Correspondingly, embodiments of the method include analyzing one or more property and taking calibration measurements of pH, total algae, and fDOM. In addition, in various embodiments the method further utilizes one or more of a turbidity sensor and a specific conductivity sensor. Correspondingly, various embodiments of the method further include analyzing one more property and taking calibration measurements of turbidity and specific conductivity.

According to various embodiments, the one or more sensors are included with a sonde. In embodiments, the sonde is a multiparameter instrument that collects water quality data with one or more sensors. Each sensor measures its parameter via, for example, electrochemical, optical, or physical detection methods. The number of sensors is not limited or is limited by the physical capacity of the sonde and embodiments of the sonde have a cluster of, for example, two or more, four or more, six or more, seven or more, or ten or more sensors. Embodiments include sensors that are user-replaceable. Depending on user-defined settings, the sonde will collect data and store it onboard the sonde, transfer the data to a data collection platform, or relay it to a user's PC via, for example, cable, USB connection, or Bluetooth connection.

As described by various embodiments in the present disclosure, the standard solution is a multiparameter standard solution that contains an aqueous pH buffer, a xanthene dye, and DSBP. Accordingly, various embodiments of the present method include verifying or calibrating at least two different types of sensors used in water quality analysis. Embodiments include simultaneously or concurrently verifying or calibrating the at least two different sensors. According to various embodiments, the method includes simultaneously contacting multiple sensors, i.e. at least two sensors, with the standard solution, analyzing the properties of the standard solution with the sensors, and taking calibration measurements. Embodiments of the method include contacting at least two different types sensors with the standard solution at the same time, concurrently analyzing corresponding properties, and taking calibration measurements of the standard solution with the sensors. Embodiments also include contacting at least two sensors with the standard solution at the same time, and then sequentially analyzing corresponding properties and taking a calibration measurement of the standard solution by one sensor followed by analyzing corresponding properties and taking a calibration measurement of the standard solution by a second sensor.

Embodiments of the method include contacting the multiple sensors separately, but simultaneously, with separate entities of the standard solution. Embodiments also include simultaneously contacting the multiple sensors together with the same entity of standard solution. By way of example, in embodiments of the present method, a pH sensor, an optical sensor for measuring total algae, and an optical sensor for measuring fDOM are together placed in contact with the standard solution. In one embodiment, the pH sensor is placed in a first vessel containing the standard solution, the optical sensor for measuring total algae is placed in a second vessel containing the standard solution, and the optical sensor for measuring fDOM is placed in a third vessel containing the standard solution. The three sensors are separately, but simultaneously, in contact with separate entities of the standard solution. In another embodiment, the three sensors are simultaneously in contact with the same entity of standard solution, for instance the three sensors are together all placed in a common vessel containing the standard solution. In either of these embodiments, the properties of the standard solution are analyzed and calibration measurements are taken concurrently or sequentially.

In another embodiment of the method, each of the multiple sensors is separately in contact with an entity of the standard solution, and the properties of the standard solution are analyzed sequentially. By way of example, the pH sensor is placed in contact with the standard solution, for instance in a vessel containing the standard solution, and a pH reading is taken. The pH sensor is then removed from contact with the standard solution (i.e. removed from the vessel), the optical sensor for measuring total algae is placed in contact with the standard solution (i.e. placed in the vessel), and a total algae reading is taken. The optical sensor for measuring total algae is then removed and replaced with the optical sensor for measuring fDOM and a fDOM reading is taken.

According to various embodiments of the disclosure, the method of verifying or calibrating a sensor used in water quality analysis includes contacting the sensor with a zero-standard solution, analyzing the zero-standard solution with the sensor, and zeroing-out the sensor based on the analysis of the zero-standard solution. Then, the steps of contacting the sensor with the standard solution, analyzing the one or more property of the standard solution with the sensor and taking a calibration measurement, and determining whether or not the sensor is calibrated based on the calibration measurement are performed.

According to various embodiments, the method of verifying or calibrating a sensor used in water quality analysis includes measuring the temperature of the standard solution and correcting the calibration measurement based on the temperature. For instance, the fluorescence intensity of many dyes have an inverse relationship with temperature and typically decrease with an increase in temperature. Embodiments of the present method account for this effect when verifying or calibrating the sensor. Embodiments of the method that utilize optical sensors to detect and measure fluorescence, such as total algae and fDOM sensors, include an additional step(s) to correct the calibration measurement based on the measured temperature of the standard solution. In some embodiments where the standard solution contains a rhodamine dye and DSBP, the relationship between temperature and the fluorescence intensity of the rhodamine dye and the fluorescence intensity of DSBP are both essentially linear. In various embodiments of the present method, correcting the calibration measurement is done by sensor software or is done by the user looking up a specific correction value that corresponds to the standard solution temperature.

According to various embodiments of the disclosure, the method of verifying or calibrating a sensor used in water quality analysis takes place in the "field." Taking place in the field, or "in situ," generally means outdoors and is meant to distinguish the present method from taking place in a controlled laboratory setting. Types of field include, for example, freshwater environments such as on or alongside rivers and lakes, or near a body of water such as a river, lake, stream, estuary, or groundwater well. It could occur, for example, on shore, on a bridge, on a boat, or at a groundwater well. It is noted that the method is not limited to taking place in the field and embodiments of the present method of verifying or calibrating a sensor take place indoors, for example in a laboratory or on a benchtop.

The present disclosure is also directed to a method of performing water quality analysis. Embodiments of the method include contacting a sensor used in water quality analysis with a standard solution containing an aqueous pH buffer, a xanthene dye, and distyryl biphenyl (DSBP), the standard solution having one or more known property that is measurable by the sensor, analyzing the one or more property of the standard solution with the sensor and taking a calibration measurement, and determining whether or not the sensor is calibrated based on the calibration measurement. When determining that the sensor is not calibrated, the method includes adjusting the sensor and repeating the above contacting, analyzing and determining steps.

When determining that the sensor is calibrated, embodiments of the method move on to include additional steps of performing the actual water quality analysis on a sample, which include contacting the calibrated sensor with a sample for water quality analysis and analyzing the sample for water quality. In various embodiments, analyzing the sample includes determining one or more of pH, concentration of algae, and concentration of fDOM in the water sample. The source of the water is not limited and embodiments of the method include water samples taken from, for example, freshwater rivers, streams or lakes, estuaries or groundwater wells. According to various embodiments, the method of performing water quality analysis takes place in the field.

EXAMPLES

Laboratory testing was performed at the U.S. Geological Survey California Water Science Center (CAWSC) Organic Matter Research Laboratory (OMRL) in Sacramento, California Testing was performed to evaluate DSBP as an alternative standard to quinine sulfate for fDOM sensor field validation and to determine whether multiple standards used for fluorescence sensor validation could be combined in a single standard that is stable over a period of months. As such, a number of lab studies were carried out to determine the feasibility of such a product.

Equipment and Supplies
Rhodamine WT, 20% Concentrate (Turner Designs, 10-108)
Disodium 4,4'-bis(2-sulfostyryl)biphenyl (TINOPAL® CBS-X, Santa Cruz Biotechnology, SC-357340)
pH 10 aqueous buffer solution, dye-free (Inorganic Ventures, PH-10-4L)
EXO2 Multiparameter Sonde (YSI Inc., 599502-00)
EXO Total Algae Smart Sensor (YSI Inc., 599102-01)
EXO fDOM Smart Sensor (YSI Inc., 599104-01)
EXO pH Sensor (YSI Inc., 577601)
EXO Conductivity & Temperature Smart Sensor (YSI Inc., 599870)
KorEXO Version 2 software (YSI Inc.)
Cyclops7 Submersible Sensor and fDOM probe (Turner Designs, Inc.)
NIST-certified digital thermometer
AQUALOG® Benchtop Spectrafluorometer (Horiba Scientific)

Test Procedures
DSBP was mixed with rhodamine WT and dye-free pH 10 buffer solution to establish a multi-parameter standard solution for field sensor verification. This standard solution was analyzed to determine the effects of temperature and to study the long-term stability of the solution.

Stability Studies
A stock solution was prepared in an acid-cleaned 1 L volumetric flask by combining 50 mg of DSBP (TINOPAL® CBS-X), 10 mL of 20% Rhodamine WT, and 989.95 mL of dye-free pH10 aqueous buffer solution, resulting in a concentration of 50,000 parts per billion (ppb) DSBP and 2,000,000 ppb Rhodamine WT. The stock solution was mixed for 20 minutes on a magnetic stir plate (200 rpm). A working sample solution was prepared by diluting 1 mL of well-mixed stock solution into 9999 mL of dye-free pH10 aqueous buffer solution, resulting in a final concentration of 5 ppb DSBP and 200 ppb Rhodamine WT.

Subsamples of the working sample solution were analyzed with the EXO2 Multiparameter Sonde containing the EXO Total Algae Sensor, EXO fDOM Smart Sensor, EXO pH Sensor, and EXO Conductivity & Temperature Smart Sensor according to the manufacturer specifications (EXO User Manual, item 603789), using KorEXO Version 2 software, at ambient temperature.

On Day 0, the fDOM and Total Algae sensors produced fDOM and chlorophyll-a readings of 60 QSU and 25 ug/L respectively. These readings correspond well to typical measurements observed in natural waters, for example in the north central San Francisco Bay-San Joaquin Delta where summer fDOM measurements range from approximately 20-40 QSU and chlorophyll-a measurements range from approximately <1-20 ug/L. The pH sensor produced a pH reading of 10.

The working sample solution was stored in a 10 L amber HDPE bottle at ambient temperature for the duration of the test. User Manual Subsamples were poured from the gently shaken 10 L amber HDPE bottle into a conditioned calibration cup. After the sensors were immersed in the sample solution, the sonde was placed on a stir plate at low speed (150 rpm) to keep the solution homogenized during measurements. Room lights were dimmed to minimize ambient light interference. Sensor measurements were collected over a three-month period on days 0, 2, 7, 21, 34, 44, 62, 77, and 92 (see, FIG. 1).

fDOM was measured and is reported in units of QSU and RFU. Chlorophyll-a and BGA-PC fluorescence were measured and chlorophyll-a is reported in units of ug/L and RFU and BGA-PC is reported in units of RFU. Data for all sensors were acceptable when measured within a relative percent difference (RPD) of 5% from initial measurements taken at T0.

As shown in FIG. 1, DSBP measured by the fDOM sensor at T0 was 19.35 RFU and remained constant throughout the three-month testing period. The mean value was 19.42 RFU. The relative difference between the minimum measured value (18.58 RFU; T77) and the maximum measure value (20.42 RFU; T34) was 9.44%.

Similarly, rhodamine measured by the Total Algae sensor remained nearly unchanged throughout the testing period, ranging from 6.30 RFU at T0 to 6.52 RFU at T92. The mean result for rhodamine was 6.38 RFU. The relative difference between the minimum measured value (6.30 RFU; T0) and the maximum measured value (6.52; T92) was 3.43%.

Solution pH also remained stable throughout the testing period and ranged from 10.06 pH at T0 to 9.92 pH at T92. Mean pH was 9.95 pH units. The relative difference between the minimum measured value (9.63 pH; T21) and the maximum measured value (10.06 pH; T0) was 4.37%. The pH sensor was recalibrated (as described in Methods) due to drift noted during the measurement recorded on T21 (pH 9.63). After recalibration, measurements of pH remained within sensor accuracy (0.1 pH units) according to manufacturer specifications for the duration of the study time period.

Subsamples of the working sample solution were also analyzed with the Turner Cyclops7 Submersible Sensor and fDOM probe according to the manufacturers specifications. These measurements were used to validate the fDOM measurements made by the YSI EXO fDOM Smart Sensor and are reported in units of milliVolt (mV). As shown in FIG. 1, fDOM as measured by the Turner sensor remained constant throughout the three-month testing period and verified the accuracy of the YSI sensor.

Full Fluorescence Spectra Analysis

Precision of the sensor measurements were validated using a benchtop instrument to measure full fluorescence spectra over the duration of the 92-day testing period on most of the same days listed above for the stability studies. To avoid possible degradation effects of the sensors, fluorescence spectra were measured from subsamples directly poured from the 10 L source bottle into 40 mL amber glass vials. Fluorescence was measured on the subsamples at room temperature in an acid-cleaned 1 cm quartz cuvette using a spectrofluorometer equipped with a charge-coupled device (AQUALOG®, Horiba Instruments) according to the methods described by Hansen et al. (2018). Fluorescence data are expressed in Raman units (RU) (see, FIG. 2).

Benchtop fluorometers yield full spectral data (i.e. emission measured every nanometer across a range of wavelengths, e.g. 370 nm-700 nm) as opposed to sensors where the measurement window is more narrow (e.g. EXO fDOM Smart Sensor: 480 nm±40 nm, which is emission center wavelength±bandpass). Full spectral measurements on the benchtop fluorometers are also more sensitive than discrete EXO sensor measurements due to differences in the detection methods. Benchtop data were evaluated at excitation 370 nm. Measurements taken at emission peak maxima for DSBP (430 nm) and rhodamine (580 nm) were within a RPD of 5% from initial measurements taken at T0.

Figure 2:
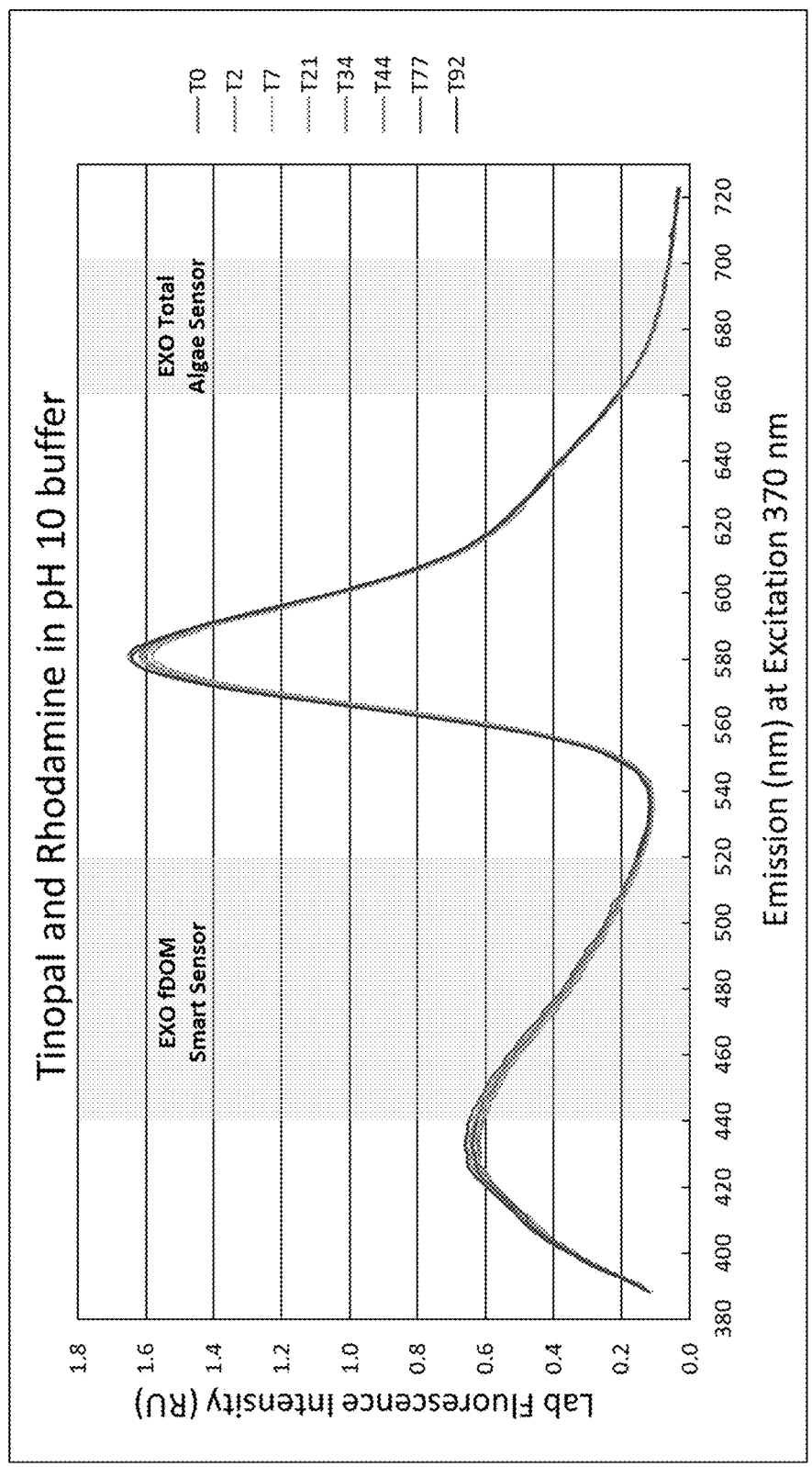
FIG. 2 is a graph of the emission spectra of DSBP and Rhodamine WT from 380 nm-720 nm at excitation 370 nm over time. Emission at excitation 370 nm (X axis); fluorescence intensity (Y axis). T=Time (day of sensor measurement); RU=Relative Units. DSBP emission peak is at 432 nm, rhodamine emission peak is at 580 nm. The measurement window for the EXO fDOM Smart Sensor (emission 480±40 nm) and EXO Total Algae Sensor (emission 685±20 nm) is indicated by vertical shaded regions.

As shown in FIG. 2, there was little to no change in the fluorescence response to DSBP over the 92-day time period. DSBP fluorescence intensity on T0 was 0.63 RU and 0.66 on T92 (mean result was 0.64 RU). The maximum measured value was 0.66 RU (T44, T92) and the minimum measured value was 0.62 RU (T2). The relative difference between the minimum and the maximum value was 5.29%.

Similar to DSBP, there was virtually no change in the fluorescence response of rhodamine over the 92-day time period. Rhodamine fluorescence intensity on T0 was 1.62 RU and 1.64 RU on T92 (mean result was 1.62 RU). The maximum measured value was 1.65 RU (T34) and the minimum measured value was 1.58 RU (T21). The relative difference between the minimum and the maximum value was 4.51%.

Temperature Correction

The sensors were submerged in an XL black bucket filled with 10 L of solution according to a modified method described in Watras et al. (2011). Both the sensors and solution were cooled in a water bath to 2° C. The bucket with sensors was then transferred to a dark incubator where it was gradually warmed to 40° C. while being constantly stirred. Simultaneous measurements of fDOM, Chlorophyll-a fluorescence, and Temperature were logged at regularly spaced time intervals as the solution warmed (see, FIG. 3 and FIG. 4)

The fDOM and Total Algae sensors detect the fluorescent components of DOM and chlorophyll-a, respectively when exposed to fluorescent light. One skilled in the art would recognize that fluorescent intensity of fDOM and chlorophyll-a is inversely related to temperature.

Figure 3:
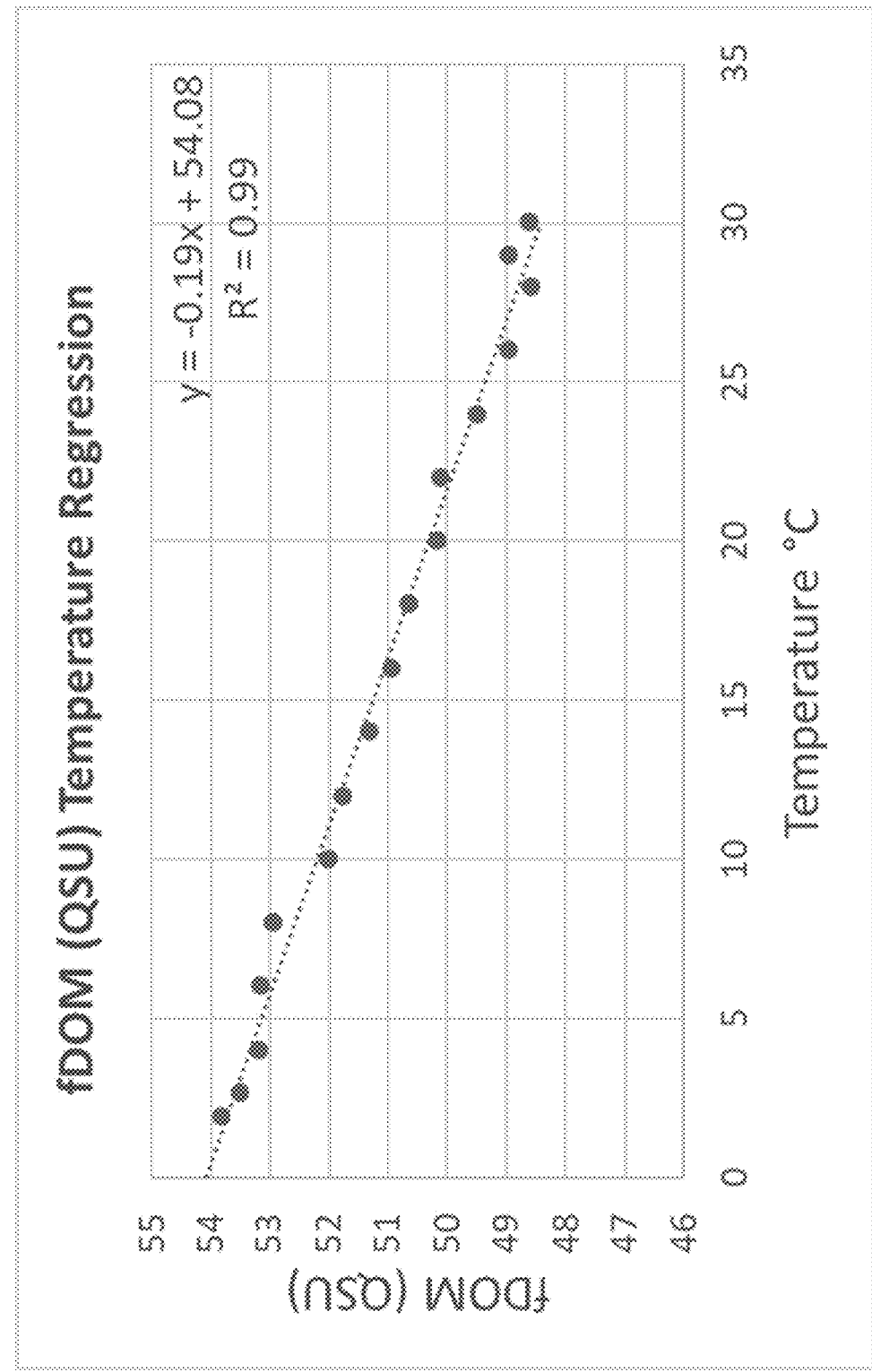
FIG. 3 is a graph of the Temperature Regression of fDOM measurement. X axis=Temperature (° C.), Y axis=fDOM (QSU).

As seen in FIG. 3, the fluorescence intensity of fDOM (QSU) measured with DSBP is inversely related to temperature in a linear manner ($R^2=0.99$) across the full range of temperatures (2° C.-40° C.).

Figure 4:
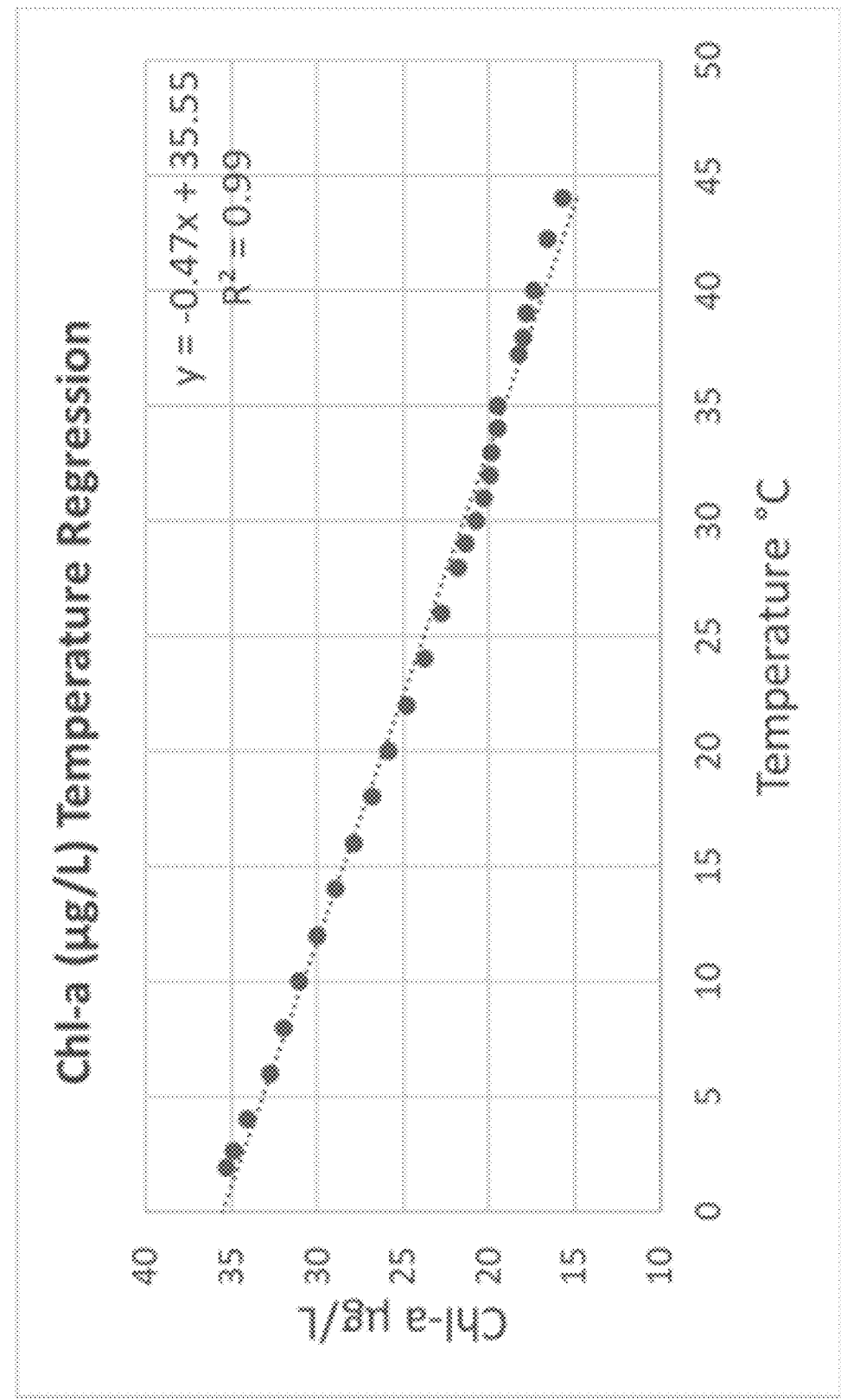
FIG. 4 is a graph of the Temperature Regression of Chlorophyll-a measurement. X axis=Temperature (° C.), Y axis=Chl-a (ug/L).

As seen in FIG. 4, the fluorescent intensity of chlorophyll-a (ug/L) measured with Rhodamine WT is inversely related to temperature in a linear manner ($R^2=0.99$) in a linear manner across the full range of temperatures (2° C.-40° C.).

Quality Assurance/Quality Control

All sensors were calibrated according to manufacturer specifications (YSI EXO User Manual) prior to the start of and during the studies. Briefly, the EXO fDOM Smart Sensor was calibrated with a two-point calibration method using laboratory reagent-grade, organic-free water (LRW; 18.2Ω) as the zero point and quinine sulfate solution prepared to a concentration of 300 QSU, which was validated using the benchtop AQUALOG® benchtop spectrafluorometer (Hansen et al., 2018). The EXO Total Algae Smart Sensor also was calibrated with a two-point calibration method using LRW (18.2 SI) as the zero point and a solution of rhodamine prepared to a concentration of 625 ug/L. The rhodamine solution was also validated on the AQUALOG® benchtop spectrafluorometer prior to its use as a calibration standard. The EXO pH sensor was calibrated using standards of pH 7 at 25° C. and pH 10 at 25° C. The EXO Conductivity & Temperature Smart Sensor was verified using a three-point temperature check at 0° C., 25° C., and 40° C. according to methods described in the U.S. Geological Survey National Field Methods (Gibs et al., 2007). Sensor results on measurement days were considered acceptable when measurements were within a relative difference of 5% from results measured at T0.

Benchtop fluorescence spectra were validated using quality-control laboratory standards (potassium dichromate and quinine sulfate) measured monthly, a laboratory standard reference material (Pure Leaf Unsweetened Black Tea) and laboratory blanks (LWR) measured daily, and laboratory replicates measured approximately every ten samples. Spectral data were inspected and considered acceptable when results were within a relative difference of 5% from results measured at T0 at peak locations of 435 nm (DSBP) and 580 nm (rhodamine).

Field Testing

The standard solution was tested in the field to investigate its suitability as a verification and calibration standard and to assess its performance with in situ sensors. Participants from several USGS Water Science Centers nationwide (Alaska, California, Caribbean-Florida, New York, Oregon) volunteered to evaluate the standard for ease of use and sensor performance to measure target values.

Approximately 1 L of standard solution—for rinsing and filling the calibration cup—is required per sonde when all three parameters are measured. Two liters of pre-measured standard solution were provided to each participant along with target values for fDOM (QSU), Chl-a (ug/L), and pH. All participants reported the solution was easy to work with and performed as expected. When user measurements were made outside a threshold of 10% from target values, the issue was identified as interference from bubbles in the solution which resulted from over shaking prior to dispensing into the calibration cup, and/or leaving the sensors immersed for too long (>5 minutes) which resulted in photodegradation of the solution. Therefore, it is recommended that the standard solution be gently combined (not over shaken) before pouring into the calibration cup to prevent bubbles from occurring. To prevent photodegradation of the solution, it is recommended that measurements be taken within 5 minutes of sensor readings or as soon as the readings stabilize, whichever occurs first, to minimize the solution's exposure to ultraviolet light.

In view of the many possible embodiments to which the principles of the present disclosure may be applied, it should be recognized that the illustrated embodiments are only examples of the present disclosure and should not be taken as limiting the scope of this disclosure. Rather the scope of the present disclosure is defined in part by the following claims.

What is claimed is:

1. A standard solution comprising: an aqueous pH buffer; a xanthene dye; and
distyryl biphenyl
(DSBP);
wherein the buffer is
from 9 to 11 wherein said solution is for verifying and calibrating water quality sensors.

2. The standard solution of claim 1, wherein the pH buffer is a pH 10 buffer.

3. The standard solution of claim 1, wherein the pH buffer is an aqueous dye-free pH 10 buffer.

4. The standard solution of claim 1, wherein the xanthene dye comprises rhodamine.

5. The standard solution of claim 1, wherein the DSBP is selected from the group consisting of 4,4'-distyryl biphenyl, disodium 4,4'-bis(2-sulfostyryl)biphenyl, and derivatives thereof.

6. The standard solution of claim 1, wherein the solution 1s a concentrated stock solution comprising:
about 10-500 parts per million (ppm) DSBP;
about 500-5000 ppm rhodamine dye; and
an aqueous pH 10 buffer.

7. The standard solution of claim 1, wherein the
solution comprises: 1-50 ppb DSBP;
10-1000 ppb rhodamine;
and an aqueous pH 10
buffer.

8. The standard solution of claim 1, wherein the solution is stable at room temperature for a period of 90 days.

9. A method of verifying or calibrating a sensor used in water quality analysis, the method comprising:
(i) contacting the sensor with a standard solution comprising an aqueous pH buffer, a xanthene dye, and distyryl biphenyl (DSBP), the standard solution having one or more known property that is measurable by the sensor;
(ii) analyzing the one or more property with the sensor and taking a calibration measurement; and
(iii) determining whether or not the sensor is calibrated based on the calibration measurement.

10. The method of claim 9, further comprising, when determining that the sensor is not calibrated, adjusting the sensor and repeating steps (i)-(iii).

11. The method of claim 9, wherein the sensor is an optical sensor.

12. The method of claim 9, wherein analyzing the one or more property of the standard solution comprises analyzing one or more of pH, total algae, fluorescent dissolved organic matter (fDOM), turbidity, and specific conductivity.

13. The method of claim 9, comprising:
contacting the sensor with a zero-standard solution, analyzing the zero-standard solution with the sensor, and zeroing-out the sensor based on analysis of the zero-standard solution; and then
performing steps (i)-(iii).

14. The method of claim 9, further comprising measuring the temperature of the standard solution and correcting the calibration measurement based on the temperature.

15. The method of claim 9, wherein the verifying or calibrating takes place in the field, and the standard solution is safely disposed of in situ.

16. The method of claim 9, comprising verifying or calibrating at least two different types of sensors used in water quality analysis.

17. The method of claim 16, wherein the at least two different types of sensors are contacted with the standard solution and simultaneously take a respective calibration measurement.

18. The method of claim 16, wherein the at least two different types of sensors are housed in a sonde.

19. A method of performing water quality analysis, the method comprising:
(i) contacting a sensor used in water quality analysis with a standard solution comprising an aqueous pH buffer, a xanthene dye, and distyryl biphenyl (DSBP), the standard solution having one or more known property that is measurable by the sensor;

(ii) analyzing the one or more property with the sensor and taking a calibration measurement;
(iii) determining whether or not the sensor is calibrated based on the calibration measurement;
(iv) when determining that the sensor is not calibrated, adjusting the sensor and repeating steps (i)-(iii), and when determining that the sensor is calibrated, performing steps (v-vi);
(v) contacting the calibrated sensor with a sample for water quality analysis; and
(vi) analyzing the sample for water quality.

20. The method of claim 19, wherein (vi) analyzing the water sample comprises determining one or more of pH, concentration of algae, and concentration of dissolved organic matter in the water sample.

* * * * *